US010563237B2

(12) United States Patent
Wirtz et al.

(10) Patent No.: US 10,563,237 B2
(45) Date of Patent: Feb. 18, 2020

(54) METHOD FOR OBTAINING SUGAR DERIVATIVES

(71) Applicant: ANNIKKI GMBH, Graz (AT)

(72) Inventors: Dörthe Hendrike Wirtz, Köln (DE); Bernd Mayer, Graz (AT)

(73) Assignee: ANNIKKI GMBH, Graz (AT)

( * ) Notice: Subject to any disclaimer, the term of this patent is extended or adjusted under 35 U.S.C. 154(b) by 0 days.

(21) Appl. No.: 14/440,022

(22) PCT Filed: Nov. 8, 2013

(86) PCT No.: PCT/EP2013/073411
§ 371 (c)(1),
(2) Date: Apr. 30, 2015

(87) PCT Pub. No.: WO2014/076012
PCT Pub. Date: May 22, 2014

(65) Prior Publication Data
US 2015/0291988 A1  Oct. 15, 2015

(30) Foreign Application Priority Data

Nov. 14, 2012  (AT) .............. A 50511/2012

(51) Int. Cl.
*C12P 19/02* (2006.01)
*C12P 7/50* (2006.01)
*C12P 7/42* (2006.01)

(52) U.S. Cl.
CPC .......... *C12P 19/02* (2013.01); *C12P 7/42* (2013.01); *C12P 7/50* (2013.01); *C12P 2201/00* (2013.01)

(58) Field of Classification Search
CPC .............. C08L 23/06; C08L 2205/025; C08L 2205/03; C08L 93/04; C08L 23/0853; C08L 23/0815; C09J 123/0853; C09J 123/0815; C09J 11/06; C09J 11/08; A61K 2300/00; A61K 35/741; A61K 31/70; A61K 31/7052; A61K 39/39558; A61K 9/0031; A61K 2035/115; A61K 31/7004; A61K 31/7016; A61K 31/715; A61K 35/39; A61K 35/74; A61K 35/742; A61K 35/744; A61K 35/745; A61K 35/747; A61K 38/46; A61K 9/0053; A61K 9/19; A61K 31/704; A61K 45/06; A61K 47/48507; A61K 47/64; A61K 47/6803; A61K 47/6809; A61K 47/6849; A61K 31/716; A61K 2039/505; A61K 31/702; A61K 31/7056; A61K 31/733; A61K 47/26; A61K 9/0019; A61K 9/0073; A61K 36/258; A61K 38/00; A61K 8/60; A61K 8/602; A61K 9/0029; A61K 9/0095; C07C 31/20; C07C 209/16; C07C 29/149; C07C 29/60; C07C 51/235; C07C 51/377; C07C 211/12; C07C 55/14; C07C 59/285; C12N 9/0006; C12N 9/0028; C12N 9/1007; C12N 9/88; C12N 15/52; C12N 9/0008; C12N 9/0067; C12N 9/10; C12N 9/12; C12N 9/54; C12N 9/92; C12Y 101/02007; C12Y 101/01224; C12Y 101/01244; C12Y 105/0102; C12Y 201/01; C12Y 201/0109; C12Y 402/01; C12Y 101/03013; C12Y 102/99003; C07D 207/12; C07D 471/04; C07D 475/04; C07H 15/26; C07H 3/02; C07H 19/16; C07H 19/167; C07H 1/00; C07H 1/06; C08G 18/3206; C08G 63/06; C08G 63/12; C08G 63/66; C08G 69/26; C08K 5/053; C08K 5/151; C09C 1/48; C09C 1/56; C12P 19/02; C12P 7/18; C12P 7/24; C12P 3/00; C12P 5/026; C12P 7/10; C12P 7/40; C01B 3/00; C08F 36/06; C08F 36/14; C12R 1/125
See application file for complete search history.

(56) References Cited

U.S. PATENT DOCUMENTS

| | | | |
|---|---|---|---|
| 2,463,784 | A | 3/1949 | Lockwood |
| 3,523,911 | A | 8/1970 | Funk et al. |
| 5,084,104 | A | 1/1992 | Heikkila et al. |
| 5,464,514 | A | 11/1995 | Pluim et al. |
| 6,187,570 | B1 | 2/2001 | Genders et al. |
| 6,284,904 | B1 | 9/2001 | Ponnampalam |
| 7,498,430 | B2 | 3/2009 | Hollingsworth |
| 7,932,063 | B2 | 4/2011 | Dunson, Jr. et al. |

(Continued)

FOREIGN PATENT DOCUMENTS

| | | |
|---|---|---|
| AT | 509307 | 7/2011 |
| CN | 102575268 CN | 7/2012 |

(Continued)

OTHER PUBLICATIONS

Novick et al. (1982) J. Bacteriology 149(1): 364-7.*
Alvira et al., "Pretreatment technologies for an efficient bioethanol production process based on enzymatic hydrolysis: A review.", Bioresour Technol. 101 (13): 4851-61.
Bridgwater, "Thermal processing of biomas for fuels and chemicals." Renewable Bioenergy-Technologies, Risks and Rewards 2003 (2003): 33-61.

(Continued)

Primary Examiner — Lisa J Hobbs
(74) Attorney, Agent, or Firm — Workman Nydegger

(57) ABSTRACT

A process for converting a sugar from a hemicellulose-containing material into the form of a compound having at least one ionic binding site, which is characterized in that the hemicellulose-containing material is hydrolyzed enzymatically or non-enzymatically and the obtained hydrolysate is subjected to a conversion involving at least one enzymatic step, wherein sugars are released and the released sugars are converted into compounds having at least one ionic binding site, and the use of such a process.

17 Claims, No Drawings

(56) References Cited

U.S. PATENT DOCUMENTS

| | | | |
|---|---|---|---|
| 2003/0172850 A1* | 9/2003 | Chun | C04B 24/06 |
| | | | 106/823 |
| 2006/0234363 A1 | 10/2006 | Frost | |
| 2008/0274527 A1* | 11/2008 | Soerensen | C12N 9/2402 |
| | | | 435/161 |
| 2012/0021467 A1 | 1/2012 | Zhang et al. | |
| 2012/0094331 A1* | 4/2012 | Fackler | C12P 7/10 |
| | | | 435/72 |
| 2013/0078677 A1 | 3/2013 | Fackler et al. | |

FOREIGN PATENT DOCUMENTS

| | | |
|---|---|---|
| JP | 62104586 JP | 5/1987 |
| JP | 62104588 JP | 5/1987 |
| JP | 2001245657 A | 9/2001 |
| WO | WO2006114095 | 11/2006 |
| WO | WO2007046417 | 4/2007 |
| WO | WO2007046417 A1 * | 4/2007 |
| WO | WO2010124312 | 11/2010 |

OTHER PUBLICATIONS

Chandra et al., "Substrate pretreatment: the key to effective enzymatic hydrolysis of lignocellulosics?", 2007, Adv Biochem Eng Biotechnol.108: 67-93.

Collins et al., "Xylanases, xylanase families and extremophilic xylanases", 2005, FEMS Microbiol Rev. 29(1): 3-23.

Himmel et al., "Biomass recalcitrance: engineering plants and enzymes for biofuels production", 2007, Science. 315 (5813): 804-7.

Jørgenson et al., "Enzymatic conversion of lignocellulose into fermentable sugars: challenges and opportunities", Jun. 27, 2007, pp. 119-134, Wiley Interscience.

Kamm and Kamm, "Principles of biorefineries", 2004, Appl Microbiol Biotechnol. 64(2):137-45.

Mansfield et al., "Substrate and Enzyme Characteristics that Limit Cellulose Hydrolysis", 1999, Biotechnol Prog. 15 (5): 804-816.

Mosier et al., 2005, "Features of promising technologies for pretreatment of lignocellulosic biomass", Bioresour Technol. 96(6):673-86.

Novick N J et al: "L-arabinose metabolism in Azospirillum brasiliense", Journal of Bacteriology, American Society for Microbiology, Bd. 149, No. 1, Jan. 1, 1982, p. 364-367, XP003012015.

Polizeli et al., "Xylanases from fungi: properties and industrial applications", 2005, Appl Microbiol Biotechnol. 67(5): 577-91.

Rivas et al., "Purification of xylitol obtained by fermentation of corncob hydrolysates" 2006, Agric Food Chem. 54(12): 4430-5.

Saake and Lehnen, "Lignin", 2007, Ullmann's Encyclopedia of Industrial Chemistry. Wiley-VCH Verlag GmbH & Co.

Tijmensen et al., "Exploration and possibilities for production of Fischer Tropsch liquids and power via biomass gasification", Biomass and Bioenergy 23 (2002) 129-152.

Watanabe et al., "L-Arabinose 1-dehydrogenase: a novel enzyme involving in bacterial L-arabinose metabolism", 2005; Nucleic Acids Symp Ser (Oxf). (49):309-10.

Watanabe et al., "Identification and Characterization of I-Arabonate Dehydratase, I-2-Keto-3-deoxyarabonate Dehydratase, and I-Arabinolactonase Involved in an Alternative Pathway of I-Arabinose Metabolism", J Biol Chem. 281(44):33521-36, 2006.

Watanabe et al., "A novel alpha-ketoglutaric semialdehyde dehydrogenase: evolutionary insight into an alternative pathway of bacterial L-arabinose metabolism", 2006, J Biol Chem. 281(39):28876-88.

Wei et al., "Purification and crystallization of xylitol from fermentation broth of corncob hydrolysates" 2010; Frontiers of Chemical Engineering in China 4(1): 57-64.

IPRP cited in PCT Application No. PCT/EP2013/073411 dated May 19, 2015.

Alvaro et al., "L-Arabinose Metabolism in Herbaspirillum seropedicae", Journal of Bacteriology, Sep. 1989, pp. 5206-5209.

Johnsen et al."D-Xylose Degradation Pathway in the Halophilic Archaeon *Haloferax volcanni*", The Journal of Biological Chemistry, vol. 284, No. 40, pp. 27290-27303, Oct. 2, 2009.

Chen, et al. "Chromatographic separation of glucose, xylose and arabinose from lignocelluosic hydrolysates using cation eschange resin" Separation and Purification Technology, 195 (2018) pp. 288-294.

Nidetzky, et al. "Continuous Enzymatic Production of Xylitol with Simultaneous Coenzyme Regeneration in a Charged Membrane Reactor" Biotechnology and Bioengineering, vol. 52 (1996) pp. 387-396.

* cited by examiner

METHOD FOR OBTAINING SUGAR DERIVATIVES

The present invention relates to a process for obtaining sugar derivatives from a hemicellulose-containing material.

In recent years, a rethinking with regard to renewable raw materials has occurred. The attempt is made to switch from a fossil raw material to a renewable raw material as a source of energy and chemical products. A renewable raw material ("nachwachsender Rohstoff"—in the following abbreviated as "Nawaro") includes an agricultural and forestry raw material of a plant or animal origin which is not used as a foodstuff or fodder. It may be utilized in a material way, but also energetically. Nawaros have many advantages such as the protection of fossil raw materials, which are provided only to a limited extent, sufficient availability and the opening of new markets for the surplus production in agriculture.

Lignocellulose is also gaining in importance as a Nawaro (Kamm and Kamm 2004, *Appl Microbiol Biotechnol.* 64(2): 137-45). It consists of 3 different chemical main fractions: cellulose, a C6 polymer made of glucose units; hemicellulose consisting of different C5 sugars such as, e.g., xylose; and lignin as a phenol polymer. One possibility of utilizing the lignocellulose is gasification so that the so-called "syngas platform" is obtained. The raw material is burnt with a limited supply of oxygen in order to produce a sythesis gas rich in $CO_2$, CO, $H_2$, $CH_4$ and $N_2$ as well as tar (Bridgwater, 2003). The synthesis gas can then, in turn, be used for producing fuel and chemicals, for example, via the Fischer-Tropsch synthesis (Tijmensen et al., 2002). A second possibility is the so-called "sugar platform". Therein, the lignocellulose is at first broken down into the 3 main components, and those are then converted further into products. The xylose may be converted, for example, into xylitol or else furfural. The glucose may be used for fermentation or converted into hydroxymethylfurfural (HMF). The lignin is frequently used for energy production or simply is combusted (Saake and Lehnen, 2007, Ullmann's Encyclopedia of Industrial Chemistry. Wiley-VCH Verlag GmbH & Co).

Within the lignocellulose, the sugars are provided in tightly cross-linked polymeric structures in the form of a partially crystallized cellulose and amorphous hemicelluloses enclosing the cellulose. In the course of the cell wall synthesis, the cavities are filled up with lignin, whereby an extremely tight complex is formed. The tightness of the structures renders accessibility impossible for enzymes such as cellulases or hemicellulases, due to their relatively high molecular weight, they are unable to get into the pores (Himmel et al., 2007, *Science.* 315 (5813): 804-7). Therefore, it is necessary that, prior to the enzymatic treatment, a chemical step occurs which increases the porosity of the lignocellulose. This step is called "pretreatment" (digestion). In the digestion, the polymeric lignocellulose matrix is broken and the cellulose fibres are thus exposed so that they become accessible for enzymes. The digestion is a critical step which is described as one of the most expensive steps in biorefinery (Mosier et al., 2005, *Bioresour Technol.* 96(6):673-86). On the other hand, it also has a very large impact on subsequent steps such as hydrolysis, fermentation, downstream processes and also the waste resulting from the processes (Alvira et al., *Bioresour Technol.* 101 (13): 4851-61).

The established digestion methods are aimed either at primarily liquefying the hemicelluloses (e.g., steam explosion-, dilute acid-pretreatment) or at achieving an increase in the porosity by liquefying lignin (z.B. lime-, ammonia-pretreatment). Those methods exhibit one grave disadvantage: Either they are energy-intensive, or they proceed predominantly at temperatures of slightly below 200° C. Or else they require a costly recovery of digestion chemicals. The type of pretreatment can have a strong influence on the enzyme activity and the yield during subsequent biocatalytic processes. At high reaction temperatures, toxic decomposition products (e.g., furfural) emerge frequently, which might inhibit the yeasts in case of a directly connected ethanol fermentation (Chandra et al., 2007, *Adv Biochem Eng Biotechnol.* 108: 67-93; Mansfield et al., 1999, *Biotechnol Prog.* 15 (5): 804-816).

As a hemicellulose, xylan is a non-homogeneous polymer. Hemicelluloses comprise mainly pentoses (C5) such as D-xylose and L-arabinose, but also hexoses (C6) such as D-glucose, D-mannose and D-galactose and also sugar acids such as glucuronic acid and 4-O-methyl-D-glucuronic acid. Hemicelluloses usually have a degree of polymerization lower than 200 (Jørgensen et al., 2007). Hemicelluloses are named after the sugars of which they are composed, e.g., the arabinoglucuronoxylan contained in wheat straw which consists of the xylose backbone and contains side chains of arabinose and glucuronic acid. The xylose units may, in addition, be esterified with acetate and ferulic or coumaric acid, respectively (Polizeli et al., 2005, *Appl Microbiol Biotechnol.* 67(5): 577-91). For the enzymatic degradation of the xylan, endo-xylanases, β-xylosidases, α-glucuronidases, α-L-arabinofuranidases and esterases are required (Polizeli et al., 2005, ibidem). The endo-xylanase splits the glycosidic bond in the xylan backbone and thus reduces the substrate's degree of polymerization. The main product of hydrolysis are β-D-xylopyranosyl oligomers, but also small amounts of mono-, di- and trisaccharides. β-Xylosidases cleave the xylooligosaccharides into monomeric xylose. The remaining enzymes exhibit activity against the side chains and detach them. α-Glucuronidases separate the glucuronic acid residues from the backbone, α-L-arabinofuranidases separate the arabinose side chains. Esterases split the ester bonds of the xylan into side chains such as acetate or p-coumaric acid or, respectively, ferulic acid (Collins et al., 2005, *FEMS Microbiol Rev.* 29(1): 3-23). The splitting of the side chains is crucial so that endo-xylanase and β-xylosidase can break down the xylan completely.

Prior Art

Xylan hydrolysis serves for cleaving the sugar polymer into sugar oligomers or sugar monomers. Therein, different goals may be differentiated. In some applications, it is reasonable to cleave both sugar polymers, cellulose and xylose, into monomers. In particular, this is the case in the production of fermentable sugars from biomasses. However, in other applications, the cellulose should be preserved as a polymer, but the xylan should be cleaved into oligomers or monomers. Xylan hydrolysis can occur chemically or enzymatically. Furthermore, the xylan hydrolysis may occur simultaneously with the separation of a lignocellulosic material or in a separate step.

In U.S. Pat. No. 3,523,911, a chemical method is described in which the biomass is treated with an acidic vapour at temperatures of from 100 to 150° C., which then, during the condensation, dissolves sugar out of the material. However, in said method, a very large amount of acid is consumed, and a hydrolysate with only a very low concentration of xylose is obtained. For example, if 15% of xylan, based on the dry matter of bagasse, is hydrolyzed, the hydrolysate will contain only 3% of xylose, which can be attributed to the high amount of water absorbed during the process. The high acid consumption and the costs for the concentration of the sugar solution render the process unprofitable.

In U.S. Pat. No. 7,932,063, a method is described in which the biomass is at first digested with an aqueous ammonia-containing solution. The obtained product is then reacted with a "saccharification enzyme", a sugar-cleaving enzyme, in order to obtain fermentable sugars. The enzyme may include several activities such as glycosidase, peptidase, lipase, ligninase and esterase. In this way, it is ensured that, if possible, the entire sugar polymer which is present is broken down into monomers. Thus, a high sugar yield with a high sugar concentration of the hydrolysate is achieved. A disadvantage is the nonspecifity of the hydrolysis. This method does not involve the possibility of cleaving only the xylan in a lignocellulosic material, while preserving the cellulose as a polymer.

In AT 509 307 A1, a method is described in which a biomass, which has been digested via an alkaline alcohol solution at temperatures of below 100° C., is treated with a carbohydrate-cleaving enzyme in order to obtain sugar monomers. If, therein, a pure xylanase is used as an enzyme, only the xylan is broken down, the cellulose is preserved as a polymer. The xylose obtained from the xylan can then be converted with a xylose reductase into xylitol without a separation of the xylose from the hydrolysate being necessary. Thus, C5 sugars are obtained at high concentrations from a pretreated hemicellulose-containing biomass. However, the method involves the disadvantage that the C5 sugars from the hydrolysis, or else the reduced subsequent products, can be separated from the reaction solution only with great effort. Remnants of soluble xylan, xylooligosaccharides and enzymes or proteins, respectively, are still present in the solution. Crystallization is required for isolating xylose or xylitol from said solution.

In the literature, methods of crystallizing xylitol from hydrolysates are described as being difficult due to the low concentration (Wei et al., 2010; *Frontiers of Chemical Engineering in China* 4(1): 57-64; Rivas et al., 2006, *Agric Food Chem.* 54(12): 4430-5). In addition, a purification step must take place prior to the crystallization because of the complex composition of such hydrolysates. Rivas et al. (2006) describe a method in which a purification step is effected with activated carbon and the concentration of the xylitol is then achieved by evaporating the solvent. Wei et al. employ a purification step with activated carbon and ion exchangers before the concentration of the xylitol is increased by evaporating the solvent. In both cases, the crystallization is effected by adding ethanol in the cold. Especially the concentration of the xylitol solution by evaporating the solvent is very cost-intensive and not optimal for an industrial-scale process.

Watanabe et al. describe an arabinose metabolic pathway in microorganisms, wherein arabinose is converted into α-ketoglutarate in 5 steps independently of the phosphorylation (Watanabe et al., 2005; *Nucleic Acids Symp Ser (Oxf).* (49):309-10; Watanabe et al. *J Biol Chem.* 281(44):33521-36, 2006). At first, the sugar is oxidized to L-arabino-γ-lactone via an L-arabinose-1-dehydrogenase. During the reaction, the enzyme transfers the electrons from the substrate onto NADP$^+$ or NAD$^+$, respectively. Via the L-arabinolactonase, the L-arabino-γ-lactone is opened up to form L-arabonate. The enzyme does not require a cofactor. On the arabonate, two dehydration steps follow. The first one is catalyzed by the L-arabonate dehydratase, which converts the L-arabonate into L-2-keto-3-deoxyarabonate (L-KDA). The L-KDA dehydratase then converts the latter into α-ketoglutaric acid semialdehyde (α-KGS). The two dehydratases catalyze the reactions without a soluble cofactor, also (Watanabe et al., 2006, *J Biol Chem.* 281(39):28876-88). At the end, the semialdehyde is then oxidized to α-ketoglutarate via the α-KGS dehydrogenase. Said enzyme requires, in turn, NAD$^+$ or NADP$^+$, respectively, for the catalysis of the oxidation (Watanabe et al., 2006, ibidem). However, said conversion is not suitable for an industrial-scale application in this form, since two of the five steps require the cofactors NAD(P)$^+$ in stoichiometric amounts, which would produce very high costs.

In US 2006/0234363 A1, the arabinose metabolic pathway as described by Watanabe et al. (2006) is partly used in order to produce 1,2,4-butanetriol in microorganisms from arabinose and xylose. In doing so, the sugar is at first oxidized to lactone by means of dehydrogenase and lactonase and is hydrolyzed into the corresponding acid. Then, a dehydration on C3 occurs in the cells so that D- or, respectively, L-3-deoxy-glycero-pentulosonic acid is formed, depending on which sugar is used. Subsequently, however, a decarboxylation of the acid group takes place so that D- or, respectively, L-dihydroxybutanal is formed. Thereupon, the aldehyde on C1 is also reduced so that D- or, respectively, L-1,2,4-butanetriol is formed. Since, in this application, the operation occurs in whole cells, it is not necessary to add the stoichiometric amounts of cofactor for the redox steps. It is, however, a disadvantage that, in cells, it is generally possible to operate with lower substrate concentrations than in a cell-free system. There is also the fact that the system is not so efficient if operations occur in whole cells, since part of the sugars used contribute to the survival of the organisms and, hence, are not converted into a product.

In U.S. Pat. No. 6,284,904, a method is described which serves for the removal of organic acids such as, for example, succinate from industrial solutions such as fermentation batches or hydrolysates. In doing so, the solution is placed over an anion exchanger, which is washed under conditions in which the organic acids are not eluted. Subsequently, the organic acids are eluted by adding stronger, inorganic anions. In this way, organic anions can be isolated and also concentrated from a complex solution such as, e.g., a hydrolysate.

In U.S. Pat. No. 6,187,570, a method is described by means of which derivatives of gluconic acid can be isolated from a fermentation batch or a cell-free biocatalytic batch by electrodialysis. Several anion and cation membranes are alternately mounted between cathode and anode. The block made up of cathode, anode and intermediate membranes is filled with an electrolyte. There are "feed compartments" into which the solution, a fermentation batch or a cell-free biocatalytic batch is/are introduced. Furthermore, there are "concentration compartments" in which the acids are concentrated. The two compartments are separated from each other by an anion membrane and a cation membrane. If a voltage is applied, the negatively charged acid moves through the anion membrane into the concentration compartment, whereas the uncharged components of the solution remain in the feed compartment. In this way, the gluconic acid or the derivatives of said acid, respectively, is/are separated from neutral components and concentrated.

In U.S. Pat. No. 5,464,514, a method is described in which sugars are separated according to their varying tendency to bind to a weak acid. The separation is then effected by electrodialysis. Boric acid is chosen as the weak acid. Different sugars have a different tendency to bind to boric acid. The compound of sugar and boric acid is negatively charged and moves in the electric field, whereas the sugars which do not bind to the boric acid remain uncharged. The electrodialysis cell consists of a cathode and an anode which have been mounted between the two cation exchange membranes. Between the two cation exchange membranes, an anion exchange membrane dividing the interspace into 2 compartments is located. Compartment I is located on the cathode's side, and Compartment II is located on the anode's side. If a solution of the sugars to be separated is now introduced into Compartment I and a voltage is applied, the negatively charged ions, i.e., the sugars having bound to the boric acid, move through the anion exchange membrane into Compartment II. The uncharged sugars remain in Compartment I. The method has been tested for the separation of lactose and lactulose as well as for the separation of glucose and fructose. However, said method is based on the fact that a varying affinity of the binding to boric acid exists between the sugars. However, part of the sugars with lower affinity for boric acid will also bind the acid and, thus, move to Compartment II. Thus, a separation of the sugars is not possible, merely, the mutual ratio between the sugars changes. In case of fructose and glucose, the ratio of transfer rates was 1.4 to 1. The separation can be enhanced by several steps of electrodialysis. Boric acid and sugars can subsequently be separated from each other in a further step of electrodialysis. The method has the drawback that proper separation can only be produced by numerous steps of electrodialysis. In addition, said method does not distinguish between monomeric and dimeric or, respectively, oligomeric sugars. Proper separation can only be generated if the substances to be separated are very different with regard to their tendency to bind to boric acid. Furthermore, it is a drawback that, with the boric acid, an additional (toxic) component must be employed.

In US 2003/0172850, a composition is described which serves as an additive to cement mixes and contains (A) a lignosulfonic acid or salts thereof; an aldohexonic acid or salts thereof; a hexuronic acid or salts thereof; hexaric acids or salts thereof; or mixtures thereof; and (B) at least one aldopentonic acid or salts thereof.

DESCRIPTION OF THE INVENTION

A process has now been found which allows a direct utilization of sugars forming during the hydrolysis of a lignocellulose-containing (or, respectively, a hemicellulose-containing) material.

In one aspect, the present invention provides a process for converting a sugar from a hemicellulose-containing material, in particular obtained from a biomass, into the form of a compound having at least one ionic binding site, which is characterized in that the hemicellulose-containing material is hydrolyzed enzymatically or non-enzymatically and the obtained hydrolysate is subjected to a conversion involving at least one enzymatic step, wherein sugars are released and the released sugars are converted into compounds having at least one ionic binding site.

A process provided by the present invention is herein referred to also as a "process of (according to) the present invention".

In a process according to the present invention, both the hydrolysis of the hemicellulose-containing material and the conversion of released sugars into compounds having at least one ionic binding site may take place in one reaction batch. This means that the hydrolysate does not have to be isolated prior to the conversion of released sugars into compounds having at least one ionic binding site (one-pot reaction).

A hemicellulose-containing material which can be used in a process according to the present invention is obtainable from a lignocellulosic material, for example, through a pretreatment of a lignocellulose-containing material.

In a process according to the present invention, a "lignocellulose-containing material" comprises in particular a lignocellulose-containing biomass, for example, annual plants such as (dry) grasses, or parts of grasses, preferably grasses, straw, energy grasses such as, e.g., switch grass, elephant grass or abaca, sisal, bagasse, or atypical lignocellulose substrates such as husks, e.g., lemmas such as rice husks, particularly preferably straw, energy grasses, bagasse or husks, even more preferably straw or bagasse.

A lignocellulose-containing biomass for use in a process according to the present invention is preferably pretreated, for example, through a treatment with an alkaline aqueous alcohol solution, preferably at temperatures of from 50 to 100° C., e.g., of 100° C. and below, preferably of 85° C. and below, particularly preferably of 71° C. The solids content of the lignocellulosic material in the aqueous solution thereby preferably amounts to 1-40% by weight, for example to 3-30% by weight of the solution, and the solid is preferably provided at a consistency of 1-40% by weight, e.g., of 3-30% by weight, in particular of 5-20% by weight. An aliphatic alcohol such as a $C_{1-6}$-alcohol, particularly preferably a $C_{1-4}$-alcohol such as ethanol or isopropanol, is preferably used as an alcohol for the pretreatment. The pH-value of the alcoholic solution, which preferably ranges from 10 to 14, may be adjusted with a base, preferably an inorganic base, for example, a hydroxide such as caustic soda lye, caustic potash. The base concentration during the reaction typically ranges from 1 to 10 mol $L^{-1}$, preferably from 2 to 6 mol $L^{-1}$, even more preferably from 4.5 to 5.5 mol $L^{-1}$. Said particular embodiment of the pretreatment of a lignocellulose-containing material, which is preferably used in a process according to the present invention, is based on the realization that a material which has been treated with an aqueous basic solution comprising an alcohol, in particular a $C_{1-6}$-alcohol, and having a pH-value of from 10.0 to 14.0 and is enriched with cellulose and hemicellulose is a material more readily usable for the enzymatic degradation into carbohydrate cleavage products than a material pretreated according to a different embodiment.

The lignocellulose-containing or, respectively, hemicellulose-containing material, which is used in a process according to the present invention, is subjected to an enzymatic or non-enzymatic, preferably an enzymatic hydrolysis. A non-enzymatic hydrolysis for obtaining a sugar-containing hydrolysate may be performed according to conventional methods, e.g., through acid-catalyzed hydrolysis. For the enzymatic hydrolysis, which may occur according to known methods, suitable enzymes are used, e.g., endo-xylanases, β-xylosidases, α-arabinofuranosidases, glucuronidases, cellulases and mixtures of such enzymes.

In a process according to the present invention, the hemicellulose-containing material, which is obtained, for example, after a pretreatment as described above, is preferably used in an aqueous solution at a consistency of 1-40% by weight of dry matter.

Compounds having at least one ionic binding site include compounds which have at least one ionic binding site which is suitable for salification, such as, for example, acid groups of formula —$(COO^-)_nR''^+$, wherein R denotes hydrogen or a cation such as, e.g., an alkali or alkaline-earth cation, e.g., Na$^+$, K$^+$, Ca$^{++}$, and n denotes the charge which the cation exhibits and which depends on the valency thereof. Released sugars in a process according to the present invention which are converted into compounds having at least one ionic binding site are preferably arabinose, e.g., L-arabinose and/or xylose, e.g., D-xylose.

In a further aspect, the present invention provides a process according to the present invention which is characterized in that released sugars which are converted into compounds having at least one ionic binding site constitute either
arabinose, in particular L-arabinose,
xylose, in particular D-xylose, or
a mixture of arabinose, in particular L-arabinose, and xylose, in particular D-xylose.

The conversion of a sugar into the form of a compound having at least one ionic binding site takes place enzymatically and may occur, for example, according to the following Reaction Scheme 1, wherein the conversion of arabinose into alpha-ketoglutaric acid via enzymatic oxidation and hydrolysis into arabonic acid is shown, that is, the conversion of a sugar into a compound exhibiting an acid group. By adding appropriate cations, for example, in the form of hydroxides such as NaOH, KOH, Ca(OH)$_2$, the acid group can be converted into a salt, if desired. R$^+$ in Reaction Scheme 1 means hydrogen or, as in the illustrated case, a monovalent cation such as Na$^+$ or K$^+$.

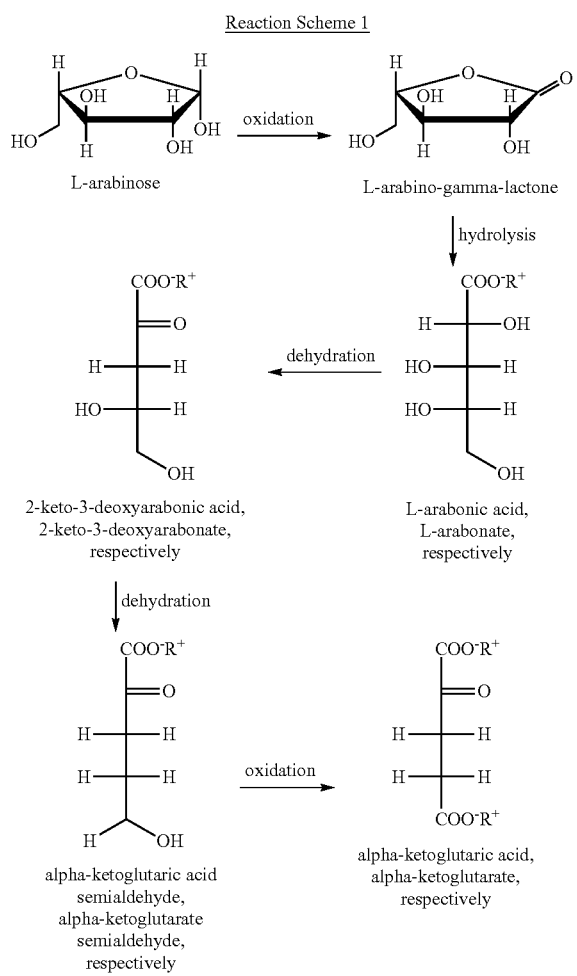

Reaction Scheme 1

In a process according to the present invention, it is an advantage that a sugar released by hydrolysis which, due to the enzymatic treatment, is provided in the form of a compound having at least one ionic binding site may be converted into desired final products directly in the hydrolysate through the application of further specific enzymes. In the above-shown reaction scheme, this is illustrated by way of the example of a conversion of arabonic acid into alpha-ketoglutaric acid or, respectively, in case it is provided as a salt, into alpha-ketoglutarate, which constitutes a valuable product in organic chemistry. In the illustrated case, enzymes which catalyze specific dehydration reactions on the arabonic acid or, respectively, secondary products thereof can be used for this purpose.

In a preferred embodiment of the process according to the present invention, the enzymatic conversion of the sugars, preferably the C5 sugars, into a compound having a ionic binding site is performed by means of an oxidoreductase into a corresponding lactone, preferably a γ-lactone. For obtaining the corresponding acid, the obtained lactone is hydrolyzed, wherein the hydrolysis may occur enzymatically, non-enzymatically and/or by spontaneous hydrolysis.

For example, a pentose dehydrogenase in combination with, for example, a lactonase and/or in combination with, for example, an alkaline hydrolysis, preferably with a hydroxide, e.g., sodium hydroxide, whereby the lactone is cleaved into the corresponding acid, is suitable as an oxidoreductase for the oxidation of C5 sugars.

In a further aspect, the present invention provides a process according to the present invention which is characterized in that released sugars, in particular C5 sugars, e.g., arabinose, are hydrolyzed by means of an oxidoreductase into a lactone, preferably a γ-lactone, e.g., arabino-γ-lactone, which is hydrolyzed into the corresponding carboxylic acid, e.g., arabonic acid, in particular through an enzymatic, non-enzymatic and/or spontaneous hydrolysis.

In order to obtain specific desired compounds, the obtained carboxylic acid, e.g., arabonic acid, may subsequently be dehydrated, for example, by means of a dehydratase, in case of L-arabonic acid, e.g., with the aid of L-arabonate dehydratase, at a desired position, in case of a C5 carboxylic acid, e.g., at position C3, so that a corresponding ketocarboxylic acid is formed, for example, in case of (L-)arabonic acid, (L-)2-keto-3-deoxyarabonic acid. If desired, the obtained ketocarboxylic acid can be dehydrated further, for example, using a dehydratase, for example, in case of a C5 carboxylic acid, at position C4, so that a ketocarboxylic acid semialdehyde is formed, for example, in case of (L-)2-keto-3-deoxyarabonic acid, using the L-2-keto-3-deoxyarabonate dehydratase of α-ketoglutaric acid semialdehyde. If desired, the obtained ketocarboxylic acid semialdehyde can be oxidized, for example, by means of an oxidoreductase in order to obtain a dicarboxylic acid; in case of a α-ketoglutaric acid semialdehyde, e.g., with the aid of a α-ketoglutarate semialdehyde dehydrogenase in order to obtain α-ketoglutaric acid.

In a further aspect, the present invention provides a process according to the present invention which is characterized in that a carboxylic acid, which has been obtained according to the present invention, e.g., arabonic acid, is dehydrated to a ketocarboxylic acid, e.g., 2-keto-3-deoxyarabonic acid, for example, by means of a dehydratase, and that, in a further aspect, a ketocarboxylic acid, which has been obtained according to the present invention, is dehydrated further to a ketocarboxylic acid semialdehyde, e.g., α-ketoglutaric acid semialdehyde, for example, by means of a dehydratase, and that, in a further aspect, the ketocarboxylic acid semialdehyde, which has been obtained according to the present invention, is oxidized to a dicarboxylic acid, e.g., α-ketoglutaric acid, for example, by means of an oxidoreductase.

In a process according to the present invention, a "keto-carboxylic acid semialdehyde" is understood to be an aliphatic compound in which a terminal C atom is provided as a carboxyl group, a different terminal C atom is provided as a formyl group and one of the remaining C atoms is provided as a keto group.

The redox cofactor(s) NADH and/or NADPH, which has/have been reduced by one or several oxidoreductases, may be converted into the oxidized state $NAD^+$ and/or $NADP^+$ by means of at least one further oxidoreductase activity, preferably in the same reaction batch. In this connection, $NAD^+$ denotes the oxidized form and NADH denotes the reduced form of nicotinamide adenine dinucleotide, whereas $NADP^+$ denotes the oxidized form and NADPH denotes the reduced form of nicotinamide adenine dinucleotide phosphate. For converting reduced cofactors into the oxidized form, an alcohol dehydrogenase, a xylose reductase, a lactate dehydrogenase, an oxidase, redox enzymes, which are coupled to an electrode, such as an alcohol dehydrogenase, a lactate dehydrogenase, an oxidase, or redox enzymes, which are coupled to an electrode, are suitable, for example, as an oxidoreductase activity.

In a further aspect, a process according to the present invention is provided which is characterized in that the redox cofactors NADH and/or NADPH, which are reduced by one or several oxidoreductases, is/are converted into the oxidized state $NAD^+$ and/or $NADP^+$ in the same reaction batch by means of at least one further oxidoreductase activity, in particular an alcohol dehydrogenase, a lactate dehydrogenase, a xylose reductase, an oxidase, or one or several redox enzymes, which are coupled to an electrode.

By using one or several oxidoreductase activities for converting the reduced redox cofactor(s) NADH and/or NADPH back into the oxidized state $NAD^+$ and/or $NADP^+$ in the same reaction batch, the use of large amounts of cost-intensive redox cofactor(s) is avoided so that, as a result, the process becomes economical.

A further advantage of a process according to the present invention is that the hydrolysate from the hydrolysis of the hemicellulose-containing biomass may be used directly for the conversion of the monomeric sugars without a purification or concentration thereof being necessary. The conversion of the monomeric sugars may take place directly in a mixture of sugars, e.g., different sugars, optionally non-hydrolyzed sugar polymers and, furthermore, solids which, optionally, are still present. A further advantage of the process is that the monomeric sugars can be isolated and concentrated from the hydrolysate very easily by a conversion into compounds having at least one ionic binding site. In this way, they can easily be separated from the other components, which, for example, might be non-converted xylan or xylooligosaccharides. By choosing the appropriate enzyme, also specifically only C5 sugars or only C6 sugars can be converted and separated, while all other sugars remain in the solution. In a process according to the present invention, preferably C5 sugars are converted.

In a process according to the present invention, the concentration of compounds which have accrued and have a ionic binding site can be lowered in the mixture by a separation method. Examples of such separation methods include ion-exchange chromatography, e.g., anion-exchange chromatography, and/or electrodialysis.

In a further aspect, the present invention provides a process according to the present invention in which compounds which have arisen and have a ionic binding site are separated from the reaction mixture in particular by means of ion-exchange chromatography and/or electrodialysis.

Thereby, the concentration of compounds which have arisen and have a ionic binding site is lowered in the mixture.

Such a separation may occur at any point in a process according to the present invention as soon as compounds having a ionic binding site are provided.

Sugars which are not converted in a process according to the present invention may be subjected, for example, to further enzymatic and/or non-enzymatic methods.

In a further aspect, the present invention provides the use of a process according to the present invention for obtaining arabinose, xylose, in particular arabinose, arabino-γ-lactone, arabonic acid, 2-keto-3-deoxyarabonic acid, α-ketoglutaric acid semialdehyde and/or α-ketoglutaric acid from a ligno-cellulose-containing material.

In the following examples, the temperature is indicated in degrees Celsius (° C.).

EXAMPLE 1

Enzymatic Hydrolysis of a Hemicellulose-Containing Material

Xylan is suspended in an acetate buffer with pH 4.3 at a concentration of 8% (w/v) and mixed with ACCELLE-RASE® TRIO™ of the Genencor company at a concentration of 1 g enzyme solution per 1 g of xylan. The batch is stirred at 50° C. for 24 h. The pH-value is checked and readjusted in case of a deviation of above 4.5 or below 4.1. The batch is filtered through a Büchner funnel and the filtrate (hydrolysate) is analyzed for its composition of monomers and their concentration by means of HPLC-LEX-DAD. A concentration of about 6% of xylose, 0.43% of arabinose and 0.27% of glucose is contained in the filtrate. In this way, about 85% of the xylose obtained in the xylan is obtained in a monomeric form.

EXAMPLE 2

Analysis of the Hydrolysate by HPLC

500 µl of the filtrate of the xylan hydrolysis according to Example 1 is centrifuged, and the supernatant is then passed through a 0.2 µM PVDF (poly-vinylidene-difluoride) filter and analyzed by means of HPLC-LEX-RID (Agilent Technologies Inc.). The sugars are thereby separated via a lead column (Shodex® Sugar SP0810) of Shodex Denko K.K. with a flow of 0.5 ml/min of water (VWR: HPLC Grade) at 80° C. The detection is effected by means of Agilent RID. An inline filter of Agilent Technologies Inc. and, as precolumns, a reversed-phase column (Axpak-WA-G), an anion-exchange column (Shodex® Asahipak® ODP-50 6E) and a sugar precolumn (Shodex® SP-G), each supplied by Showa Denko K.K., are used.

EXAMPLE 3

Oxidation of L-Arabinose to Arabonate by an Arabinose Dehydrogenase with Cofactor Recycling Via an Alcohol Dehydrogenase and Subsequent Hydrolysis of the Lactone by Caustic Soda Lye A 0.5 ml batch contains 50 mg/ml of arabinose, 5 U/ml of the recombinant arabinose dehydrogenase from *Burkhold-*

*eria vietnamiensis* and a mixture of 0.5 mM NADP+ and 0.5 mM NADPH. For the regeneration of the cofactor, 2.5% (w/v) acetone and 5 U/ml of the recombinant alcohol dehydrogenase from *Lactobacillus kefir* are added. The enzymes are used in the form of a cell lysate. The reaction takes place at 40° C. and pH 10 for 24 h under continuous shaking (900 rpm). After 24 h, the reaction vessel is incubated at 60° C. for 10 min in order to inactivate the enzymes. Subsequently, 5 μl of 2 M NaOH is added.

In this way, more than 60% of the L-arabinose is converted into sodium-L-arabonate. The analysis is effected with GC-MS.

EXAMPLE 4

Oxidation of L-Arabinose to Arabonate by an Arabinose Dehydrogenase with Cofactor Recycling Via an Alcohol Dehydrogenase and Subsequent Hydrolysis of the Lactone by a Lactonase A 0.5 ml batch contains 50 mg/ml of arabinose, 5 U/ml of the recombinant arabinose dehydrogenase from *Burkholderia vietnamiensis* and a mixture of 0.5 mM NADP+ and 0.5 mM NADPH. For the regeneration of the cofactor, 2.5% (v/v) acetone and 5 U/ml of the recombinant alcohol dehydrogenase from *Lactobacillus kefir* are added. The enzymes are used in the form of a cell lysate. The reaction takes place at 40° C. and pH 10 for 24 h under continuous shaking (900 rpm). After 24 h, the reaction vessel is incubated at 60° C. for 10 min in order to inactivate the enzymes. After cooling, 50 μl of an *E. coli* cell lysate is added with overexpressed L-arabinolactonase from *Azospirillum brasiliense*, and the reaction is shaken at 40° C. (900 rpm) for another 24 h. Subsequently, the reaction vessel is incubated at 60° C. for 10 min in order to inactivate the enzyme.

In this way, more than 65% of the L-arabinose is converted into L-arabonate. The analysis is effected with GC-MS.

EXAMPLE 5

Analysis of Oxidation Reactions by Means of GC-MS

For the analysis of oxidation reactions on GC-MS, substrates and products must be derivatized. The batches are centrifuged, passed through a 0.2 μM PVDF filter and diluted 1:30. 20 μl of the dilution is transferred into a 0.5 ml vial and dried in the Speedvac. For derivatization, 150 μl pyridine and 50 μl of a 99:1-mixture of N,O-bis(trimethylsilyl)-trifluoroacetamide and trimethylchlorosilane are then added. As an internal standard, sorbitol is contained in the pyridine at a concentration of 0.1 mg/ml. Derivatization takes place at 60° C. for 16 h. Subsequently, the samples are analyzed via GC-MS. In doing so, the samples are separated via the separation column HP-5ms (5%-phenyl)-methylpolysiloxane in a gas-phase chromatograph and analyzed with Shimadzu's mass spectrometer GCMS QP210 Plus.

EXAMPLE 6

Conversion of Arabinose into Arabonate/Arabinolactone in a Mixture of Xylose and Arabinose 180 mg D-xylose and 20 mg L-arabinose were dissolved together with 2 U of L-arabinose dehydrogenase from *Burkholderia vietnamiensis* as well as 2 U of D-xylose reductase from *Candida parapsilosis* to a total volume of 500 μl in 50 mM of aqueous Tris buffer (pH=7.0 at 25° C.). The reaction took place in a closed reaction vessel at 40° C. under agitation (900 rpm, Eppendorf Thermomix®). After 30 min, the enzymes were inactivated by 15 minutes of incubation at 65° C., denatured proteins were separated by centrifugation (21000 g, 5 min), and the sugars were quantified by means of GC-MS. The employed L-arabinose was converted completely, 92% of it into L-arabonate or L-arabino-γ-lactone and the remaining 8% into L-arabitol. About 89.5% of the employed D-xylose remained, while 10.4% was converted into xylitol. <0.1% of the employed D-xylose was oxidized to D-xylonate/D-xylono-γ-lactone.

The relatively selective conversion of arabinose into arabonate/arabinolactone as achieved in this case results from the higher specific activity of the arabinose dehydrogenase for arabinose in comparison to xylose, from the relative proportions of arabinose and xylose in the reaction mixture as well as from the limited enzyme activity/reaction time.

The example shows, among other things, that specific sugars can be separated from a sugar mixture by means of a process according to the present invention.

The invention claimed is:

1. A process for converting a sugar from a hemicellulose-containing material into a compound having at least one ionic binding site, the process comprising:
   providing a hemicellulose-containing material from an annual plant including arabinose and xylose;
   hydrolysing the hemicellulose-containing material enzymatically or non-enzymatically to obtain a hydrolysate, the hydrolysate including arabinose and xylose as released sugars;
   subjecting the obtained hydrolysate to a conversion in a reaction mixture involving at least one enzymatic step, the conversion comprising converting at least a portion of the released sugars into a compound having at least one ionic binding site, by:
   oxidizing the arabinose in a first redox reaction by means of a first oxidoreductase into arabino-γ-lactone, and
   hydrolysing said arabino-γ-lactone to arabonic acid,
   wherein the conversion involves redox cofactors comprising at least one of NADH/NAD+ or NADPH/NADP+, at least one of NAD+ or NADP+ being reduced to NADH or NADPH as part of the first redox reaction involving the first oxidoreductase and the arabinose,
   and at least one of NADH or NADPH being oxidized to NAD+ or NADP+ in a second redox reaction carried out in the reaction mixture by means of a xylose reductase, the xylose reductase being different from the first oxidoreductase, and wherein the xylose reductase reduces at least a portion of the released xylose.

2. A process according to claim 1, further comprising dehydrating the arabonic acid to 2-keto-3-deoxyarabonic acid.

3. A process according to claim 2, further comprising dehydrating the 2-keto-3-deoxyarabonic acid to α-ketoglutaric acid semialdehyde.

4. A process according to claim 3, further comprising oxidizing the α-ketoglutaric acid semialdehyde to α-ketoglutaric acid.

5. A process according to claim 1, wherein the compound having at least one ionic binding site is separated from the reaction mixture by means of ion-exchange chromatography and/or electrodialysis.

6. A process according to claim 1, wherein the hemicellulose-containing material is formed by treating a lignocellulosic material from the annual plant with an alkaline aqueous alcohol solution.

7. A process according to claim 1, wherein the arabinose is L-arabinose and the xylose is D-xylose.

8. A process according to claim 3, wherein the arabonic acid is dehydrated to 2-keto-3-deoxyarabonic acid by means of a dehydratase.

9. A process according to claim 3, wherein the 2-keto-3-deoxyarabonic acid is dehydrated further to α-ketoglutaric acid semialdehyde by means of a dehydratase.

10. A process according to claim 4, wherein the α-ketoglutaric acid semialdehyde is oxidized to α-ketoglutaric acid by means of an oxidoreductase.

11. A process according to claim 6, wherein the lignocellulosic material is treated with an alkaline aqueous alcohol solution at a temperature in a range of 50° C. to 100° C.

12. A process for converting a sugar from a hemicellulose-containing material into a compound having at least one ionic binding site in a single reaction mixture process, the process comprising:
providing a hemicellulose-containing material from an annual plant including xylose and arabinose;
hydrolysing the hemicellulose-containing material to obtain a hydrolysate, the hydrolysate including released arabinose and xylose sugars;
without prior isolation of the released arabinose and xylose sugars, converting at least a portion of the released arabinose into a compound having at least one ionic binding site, the conversion comprising:
oxidizing the arabinose into arabino-γ-lactone using an arabinose dehydrogenase and one or more redox cofactors; and
hydrolysing the arabino-γ-lactone to arabonic acid using at least one of an arabinolactonase or an alkaline hydrolysis process,
wherein the one or more redox cofactors include at least one of NADH/NAD+ or NADPH/NADP+, the one or more redox cofactors being reduced in the single reaction mixture during the oxidation of the arabinose, and the one or more redox cofactors being oxidized in the single reaction mixture through action of a xylose reductase and in combination with a reducible organic compound.

13. The process of claim 12, further comprising dehydrating the arabonic acid to 2-keto-3-deoxyarabonic acid using an arabonate dehydratase.

14. The process of claim 13, further comprising dehydrating the 2-keto-3-deoxyarabonic acid to an α-ketoglutaric acid semialdehyde using a 2-keto-3-deoxyarabonate dehydratase of α-ketoglutaric acid semialdehyde.

15. The process of claim 4, further comprising oxidizing the α-ketoglutaric acid semialdehyde to an α-ketoglutaic acid using an α-ketoglutarate semialdehyde dehydrogenase.

16. The process of claim 14, wherein the reducible organic compound comprises the xylose.

17. The process of claim 5, wherein the compound having at least one ionic binding site is selected form arabonic acid, 2-keto-3-deoxyarabonic acid, α-ketoglutaric acid semialdehyde, α-ketoglutaric acid, or a mixture thereof, and wherein all other sugars and other components remain in the solution of the hydrolysate.

* * * * *